United States Patent [19]

Makovec et al.

[11] Patent Number: 5,232,937
[45] Date of Patent: Aug. 3, 1993

[54] DERIVATIVES OF N-PHENYLBENZAMIDE WITH ANTI-ULCER AND ANTI-ALLERGY

[75] Inventors: Francesco Makovec, Monza; Walter Peris, Milan; Angelo L. Rovati, Monza, all of Italy

[73] Assignee: Rotta Research Laboratorium SpA., Milan, Italy

[21] Appl. No.: 752,435

[22] PCT Filed: Feb. 19, 1990

[86] PCT No.: PCT/EP90/00270
§ 371 Date: Aug. 19, 1991
§ 102(e) Date: Aug. 19, 1991

[87] PCT Pub. No.: WO90/09989
PCT Pub. Date: Sep. 7, 1990

[30] Foreign Application Priority Data

Feb. 22, 1989 [IT] Italy ............................ 67119 A/89

[51] Int. Cl.$^5$ ............... C07D 257/04; A61K 31/185; C07C 233/81; C07C 235/56
[52] U.S. Cl. ..................... 514/381; 514/522; 514/563; 558/393; 562/435; 562/450; 548/253; 564/153
[58] Field of Search ............... 558/393; 562/435, 450; 548/253; 514/381, 522, 563

[56] References Cited

U.S. PATENT DOCUMENTS 4,703,110 10/1987 Shudo ........................... 534/566
4,927,928 5/1990 Shroot ........................... 544/154

Primary Examiner—Robert Gersil
Attorney, Agent, or Firm—Sughrue, Mion, Zinn, Macpeak & Seas

[57] ABSTRACT

Derivatives of N-phenylbenzamide with general formula (1) in which $R_1$ is a cyano, nitro, halogen, hydrozy, $C_1$–$C_4$ alkyl methyl, methoxy or tetrazol-5-yl group, $R_2$ is hydrogen, hydroxy, or methoxy, $R_3$ is a tetrazol-5-yl group or hydrogen, $R_4$ and $R_5$ are hydrogen if $R_3$ is tetrazolyl but are independently selected from the group consisting of carboxy, methoxycarbonyl, ethoxycarbonyl and carbamoyl if $R_3$ is hydrogen, and $R_6$ is hydrogen or methyl. The derivatives have an anti-ulcer and anti-allergy activity.

8 Claims, No Drawings

DERIVATIVES OF N-PHENYLBENZAMIDE WITH ANTI-ULCER AND ANTI-ALLERGY

The subject of the present invention is original derivatives of N-phenylbenzamide which can be represented by the general formula indicated below:

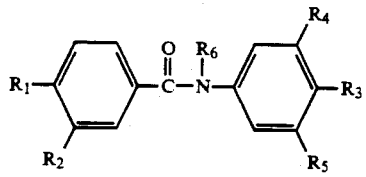

in which
$R_1$ is a cyano, nitro, halogen, hydroxy, $C_1$–$C_4$ alkyl, methoxy or tetrazol-5-yl group
$R_2$ is hydrogen, hydroxy, or methoxy
$R_3$ is a tetrazol-5-yl group or hydrogen
$R_4$ and $R_5$ are hydrogen if $R_3$ is tetrazolyl or $R_4$ and $R_5$ are independently selected from the group consisting of carboxy, methoxycarbonyl, ethoxycarbonyl and the carbamoyl if $R_3$ is hydrogen, and $R_6$ is hydrogen or methyl and their pharmaceutically acceptable salts.

These compounds show interesting pharmacological properties in mammals. One of these properties consists of a high degree of regulatory activity on gastric secretion, particularly activity against the secretion of acid when the secretion is stimulated by various agents such as histamine, carbachol and pentagastrin. Another property consists of a protective and healing activity in relation to the gastro-enteric mucous membrane. A further property is that of inhibiting the release of chemical mediators responsible for allergic or immunological reactions. These compounds can thus be used to advantage in the treatment of various disorders in man such as disorders of the digestive system, such as those resulting from gastro-secretory disorders or lesions, that is peptic ulcers, gastro-duodenitis or colitis; or may be used to treat various pathological conditions which can be attributed to hypersensitivity to allergens such as, for example, bronchial asthma, rhinitis, or allergic conjunctivitis or other pathological conditions of other organs or areas.

The method for the preparation of the N-phenylbenzamide derivatives of the invention is characterised by various steps which can be represented as follows:

a) in the case of compounds in which the $R_4$ and $R_5$ substituents are independently selected from carboxy, methoxycarbonyl, ethoxycarbonyl and carbamoyl groups and the $R_3$ substituent is hydrogen, reacting 1-$R_4$-3-$R_5$-5-amino-phenyl wherein $R_4$ and $R_5$ have the above meaning in an equimolar ratio with the chloride of the suitably-$R_1$, $R_2$-substituted benzoic acid, in which $R_1$ and $R_2$ have the meanings given above, at a temperature of between about $-5°$ C. and about $+20°$ C., preferably about $+5°$ C., in the presence of an alkali metal or alkaline-earth metal hydroxide, carbonate or bicarbonate (which serves both to salify the carboxyl functions of the 5-amino-isophthalic acid and as an acceptor of hydrochloric acid) or in the presence of a tertiary organic base. The acid chloride can be added as it is or dissolved in a solvent miscible with water (e.g. dioxan, acetone, tetrahydrofuran). The reaction time may vary from about half an hour to 24 hours; the reaction can generally be considered to be complete after 12 hours. At this point the reaction mixture is acidified and the desired products are isolated by filtration and purified by crystallisation.

b) in the case of compounds in which the $R_4$ and $R_5$ substituents are both hydrogen, the $R_3$ substituent is the tetrazol-5-yl group and in which $R_1$ and $R_2$ have the meanings given above, except in the case in which $R_1$ is the tetrazol-5-yl group, reacting 5-(p-amino-phenyl)-tetrazole with the stoichiometric quantity of the chloride of the suitably-substituted benzoic acid dissolved in a solvent miscible with water, preferably tetrahydrofuran, between about $-5°$ C. and about $20°$ C., preferably at about $+5°$ C. in the presence of a tertiary organic base. The reaction time may vary from about half an hour to 24 hours; in this case also, the reaction can generally be considered to be complete after 12 hours. The solvent is then evaporated under vacuum, the residue taken up with $H_2O$ and acidified with dilute HCl. The desired products are isolated by filtration, washed until neutral and purified by crystallisation.

c) alternatively, for compounds in which the $R_4$ and $R_5$ substituents are independently selected from carboxy, methoxycarbonyl, ethoxycarbonyl and carbamoyl groups, $R_3$ is hydrogen, $R_2$ has the meaning given above and $R_1$ is a tetrazol-5-yl group, the corresponding compound having the cyano group at $R_1$ and produced as described in point a) is converted by reaction under hot conditions with sodium azide and ammonium chloride in a high-boiling solvent, preferably dimethylformamide, at a temperature of between 60° and 140° C. (preferably 100° C.). The reaction time varies between 8–36 h but, on average, 24 hours are sufficient to complete the reaction. When the reaction has finished, the reaction mixture is diluted with $H_2O$ and acidified. The precipitate is filtered, washed until neutral and possibly crystallised.

d) in the case of compounds in which the $R_1$ and $R_3$ substituents are both the tetrazol-5-yl group, the $R_4$ and $R_5$ substituents are both hydrogen and the $R_2$ substituent has the meaning given above, 4-cyanoaniline is reacted with a stoichiometric quantity of the chloride of the suitably substituted benzoic acid preferably dissolved in tetrahydrofuran, in the presence of a tertiary base such as, for example, triethylamine which acts as an acceptor of hydrochloric acid, at a temperature of between 0° and 20° C., preferably about 10° C. for a time which may vary from about one hour to 24 hours; the reaction can generally be considered to be complete after 12 h. The solvent is evaporated under vacuum, the residue is taken up with $H_2O$, filtered, washed until neutral and dried.

The compound is then converted into the di-tetrazolyl derivative by reaction with sodium azide and ammonium chloride by a method similar to that described above.

The following examples are given further to illustrate the invention.

EXAMPLE 1

N-(3,5-dicarboxy)phenyl-4-cyanobenzamide (compound 1)

To a solution of 60 g (0.33 moles) of 5-amino-isophthalic acid in 660 ml of 1N NaOH kept at 5° C. are added simultaneously a further 330 ml of 1N NaOH and 54.6 g (0.33 moles) of 4-cyanobenzoyl chloride dissolved in 150 ml of acetone. The mixture was left to react under agitation for 12 hours. The mixture was acidified with dilute HCl and the precipitate was filtered and washed with $H_2O$. Purification was carried out by crystallisation from dimethylformamide (DMF)-$H_2O$.

Quantity produced 76 g.
Yield 74%.
Melting point: 324° C. (The melting points were determined by differential thermal analysis).

EXAMPLE 2

N-(3,5-dicarboxy)phenyl-4-nitrobenzamide (compound 2)

The method was carried out as in Example 1 with the use of 4-chlorobenzoyl chloride instead of 4-cyanobenzolyl chloride.
Yield 79%.
Melting point: 325° C.

EXAMPLE 3

N-(3,5-dicarboxy)phenyl-4-chlorobenzamide (compound 4)

The method was carried out as in Example 1 with the use of 4-chlorobenzoyl chloride instead of 4-cyanobenzoyl chloride.
Yield 75%.
Melting point: 347° C.

EXAMPLE 4

N-(3,5-dicarboxy)phenyl-4-methylbenzamide (compound 4)

The method was carried out as in Example 1 with the use of 4-methylbenzoyl chloride instead of 4-cyanobenzoyl chloride.
Yield 83%.
Melting point: 340° C.

EXAMPLE 5

N-(3,5-dicarboxy)phenyl-4-methoxybenzamide (compound 5)

The method was carried out as in Example 1 with the use of 4-methoxybenzoyl chloride instead of 4-cyanobenzoyl chloride.
Yield 72%.
Melting point: 329° C.

EXAMPLE 6

N-(3,5-dicarboxy)phenyl-3-hydroxy-4-nitrobenzamide (compound 6)

The method was carried out as in Example 1 with the use of 3-hydroxy-4-nitrobenzoyl chloride instead of 4-cyanobenzoyl chloride.
Yield 79%.
Melting point: 320° C.

EXAMPLE 7

N-(3,5-dicarboxy)phenyl-3,4-di-hydroxybenzamide (compound 7)

The method was carried out as in Example 1 with the use of 3,4 diacetoxybenzoyl chloride instead of 4-cyanobenzoyl chloride. The crude diacetyl derivative thus obtained was dissolved in tetrahydrofuran with the addition of 2 moles of 2N NaOH, left to react for 12 h at 20° C., acidified with dilute HCl, filtered, washed until neutral and crystallised from DMF-$H_2O$.
Yield 73%.
Melting point: 322° C.

EXAMPLE 8

N-(3,5-dicarboxy)phenyl-3,4-dimethoxybenzamide (compound 8)

The method was carried out as in Example 1 with the use of 3,4-dimethoxybenzoyl chloride instead of 4-cyanobenzoyl chloride.
Yield 78%.
Melting point 333° C.

EXAMPLE 9

N-(3,5-dicarboxy)phenyl-3-methoxy-4-nitrobenzamide (compound 9)

The method was carried out as in Example 1 with the use of 3-methoxy-4-nitrobenzoyl chloride instead of 4-cyanobenzoyl chloride.
Yield 80%.
Melting point: 332° C.

EXAMPLE 10

N-°4-(5-tetrazolyl)é-phenyl-4-cyanobenzamide (compound 10)

The method was carried out as in Example 1 with the use of 5-(p-aminophenyl)-tetrazole (prepared as described by Van Straaten et al, —Rec. des Trav. Chim. Paybas-77 (1958), 1129–1134) instead of 5-amino-isophthalic acid.
Yield 70%.
Melting point: 284° C.

EXAMPLE 11

N-(3,5-dicarboxy)phenyl-4-(5-tetrazolyl)-benzamide (compound 11)

9.7 g (0.18 moles) of ammonium chloride and 10.9 g (0.17 moles) of sodium azide were added to a suspension of 26 g (0.0838 moles) of N-(3,5-dicarboxy)phenyl-4-cyanobenzamide (compound 1) in 300 ml of dimethylformamide. The mixture was left to react at 100° C. under agitation for 24 h. The mixture was diluted with water, acidified with dilute hydrochloric acid and the preparation formed was filtered and washed with $H_2O$. Purification was carried out by crystallisation from dimethylformamide-$H_2O$.

Quantity produced: 24.3 g.
Yield 82%.
Melting point: 303° C.

EXAMPLE 12

N-(4-cyanophenyl)-4-cyanobenzamide 13.1 g (0.13 moles) of triethylamine were added to a solution of 14.2 g (0.12 moles) of 4-aminobenzonitrile in 100 ml of tetrahydrofuran and the temperature was then kept at about 5° C. and 20 g (0.12 moles) of 4-cyanobenzoyl chloride were added dropwise. The mixture was left to react for 12 h under agitation. The solvent was evaporated, the residue was taken up with $H_2O$ and the precipitate formed was filtered. The precipitate was washed with dilute HCl, a 10% solution of bicarbonate and again with $H_2O$.

Product 27 g.
Yield 91%.
Melting point: 265° C.

EXAMPLE 13

N-°4-(5-tetrazolyl)phenyl-4-(5-tetrazolyl)-benzamide (compound 12)

g (0.32 moles) of sodium azide and 18.7 g (0.35 moles) of ammonium chloride were added to a suspension of 20 g (0.08 moles) of N-(4-cyano)-phenyl-4-cyano-benzamide (Example 12) in 300 ml of dimethylformamide. The method of Example 11 was then used.

Product 19.2 g.
Yield 72%.
Melting point: 301° C.

EXAMPLE 14

N-(3-carboxy-5-carbamoyl)phenyl-4-cyanobenzamide (compound 13)

33.1 g (0.2 moles) of 4-cyanobenzoyl chloride dissolved in 100 ml of acetone and 18.5 g (0.22 moles) of sodium bicarbonate dissolved in 100 ml of $H_2O$ were added simultaneously to a solution of 39.4 g (0.2 moles) of the ammonium salt of 5-amino-3-carbamoyl benzoic acid in 200 ml of water kept at 5° C. The mixture was left to react under agitation for 12 h. The mixture was acidified with dilute HCl and the precipitate was filtered and washed with $H_2O$. Purification was carried out by crystallisation from DMF-$H_2O$.

Product 43.9 g.
Yield 71%.
Melting point 341° C.

5-amino-3-carbamoyl benzoic acid was prepared by the reduction of 3-carbomethoxy-5-nitro-benzoic acid dissolved in ethanol under a pressure of 4 atmospheres of hydrogen, in the presence of platinum oxide as a catalyst, to give 3-carbomethoxy-5-aminobenzoic acid (melting point 236° C. as the hydrochloride) which was converted into the corresponding 3-carbamoyl derivative by treatment with excess concentrated ammonia at 5° C. The compound was isolated as the ammonium salt (melting point 130° C.) by the precipitation of the reaction mass with acetone.

EXAMPLE 15

N-(3-carboxy-5-carbamoyl)phenyl-4-(5-tetrazolyl)-benzamide (compound 14)

The method was carried out as in Example 11 with the use of compound 13 instead of compound 1.
Yield 77%.
Melting point 314° C.

The antisecretive activities of the products of the invention and their protective activity as regards the mucous membranes were determined by various experimental models as described below.

The anti-secretive activities were determined in rats with the use of male animals weighing approximately 200 g, anaesthetised with urethane. Gastric secretion was stimulated with pentagastrin, histamine or cabachol. The method of K. S. Lai °Gut 5, (1964), 327–341é, slightly modified, was used.

After tracheotomy, cannulae were inserted in the aesophagus and the duodenum. These were perfused with a tepid solution (37° C.) which was passed through the stomach at a constant flow rate of 1 ml/minute by means of a peristaltic pump. After stabilisation for 20 minutes, the stimulant, dissolved in a physiological solution, was perfused for 120 minutes at the dose indicated in Table 1 in a volume of 0.95 ml/hour. After 60 minutes of perfusion (base stimulation) the product under test was administered intravenously (I.V.) in a bolus and the perfusion of the stimulant was continued for a further 60 minutes. The acid secretion was recorded continuously as a function of time.

The activity of the product was evaluated as a percentage reduction in the acid secreted after the administration of the product against the base acidity measured in the first 60 minutes of collection which was in the presence of the stimulant alone.

The antagonistic compounds tested were administered at different doses so as to enable ED50 values to be calculated, that is, the dose (in mg/kg I.V.) which can reduce the effect of the various secretion stimulants by 50%.

The results obtained are given in the following table in which the activities of the compounds are expressed as ED50 values in the three different situations studied, that is, under the stimulus of pentagastrin, histamine and carbachol in the doses indicated in the Table.

TABLE 1

Antagonistic activity (ED50 mg/kg I.V.) towards secretion induced by various agents in rats.

| COMPOUND | ED50 mg/kg | | |
|---|---|---|---|
| | Pentagastrin (30 mcg/kg/h) | Histamine (2.3 mg/kg/h) | Carbachol (30 mcg/kg/h) |
| 1 | 50 | 47 | 33 |
| 2 | 91 | 109 | 68 |
| 3 | 115 | 108 | 104 |
| 4 | 189 | IN (>250) | 216 |
| 5 | 223 | 240 | IN (>250) |
| 6 | 210 | 205 | 186 |
| 7 | 97 | 102 | 90 |
| 8 | 208 | 222 | 188 |
| 9 | 88 | 100 | 88 |
| 10 | 42 | 45 | 39 |
| 11 | 33 | 41 | 50 |
| 12 | 26 | 32 | 30 |
| 13 | 68 | 73 | 65 |
| 14 | 51 | 48 | 48 |

The anti-secretive activity appears particularly noteworthy in the compounds in which $R_1$ is a strongly electron-attractive substituent such as, for example, nitro, cyano and tetrazol-5-yl. This activity is even more interesting when the low toxicity of the compounds themselves is taken into account. For example compound 1 has an LD50 IV in mice of 2400 mg/kg. The toxic dose in this case is thus about 50 times greater than the antacid-secretion dose (calculated on the ED50 of pentagastrin).

Some of the compounds of the invention, which had particularly high anti-secretive activities in the Lai test described above, were examined for their gastro-protective (or cytoprotective) activities in various experimental ulcer models.

a) Alcohol and sodium chloride ulcer

Male rats weighing approximately 150 g which had been starved for 24 hours were given oral doses of 1.5 ml/animal of ethanol or alternatively, 1.5 ml of a hypertonic NaCl 25% solution. The drugs under test were administered intravenously 15 minutes before the irritant. One hour after the administration of the alcohol or of the sodium chloride, the animals were killed, the stomachs removed, opened and cut along the major curvature and examined under a microscope (10 times magnification) for necrotic lesions which were counted and classified in accordance with the method given below, which is a modification of that described in Med. Exp. 4, 284–292 (1961). It consists of the assignment of arbitrary points according to the number and gravity of the lesions in accordance with the following criterion:

1 if the length of the necrotic area is 2 mm
2 if the length of the necrotic area is between 2 and 4 mm
3 if the length of the necrotic area is 4 mm
5 if the length of the area is 4 mm with a perforated ulcer.

A lesion index is then obtained by adding the number of lesions multiplied by their respective points.

The compounds were administered intravenously (I.V.) in various doses so as to enable protective ED50 values to be calculated, that is, the dose in mg/kg IV) which is capable of reducing the gastric muscular damage induced by the lesive agent by 50%.

b) Stress ulcer

Male rats weighing approximately 150 g which had been starved for 24 hours were imprisoned in individual cylindrical cages and immersed up to the xiphoid process in cool water kept thermostatically at 19° C. The compounds were administrated intramuscularly (I.M.) 15 minutes before the start of the test.

5 hours after the start of their containment, the animals were killed, their stomachs were removed and a quantitative evaluation was then carried out as described above.

In this case the compounds were again administered in different doses so as to enable protective ED50 values to be calculated, that is, the dose in mg/kg (I.M.) capable of reducing the damage caused by the stress of containment by 50%.

The results obtained are shown in Table 2, in which the protective activities of the compounds are expressed as ED50 values in mg/kg for the different experimental conditions investigated.

TABLE 2

| | CYTOPROTECTIVE ACTIVITY IN VARIOUS EXPERIMENTAL MODELS OF ULCERS IN RATS | | |
|---|---|---|---|
| | ULCER CAUSED BY ETHANOL ED50 mg/kg I.V. | ULCER CAUSED BY 25% NaCl ED50 mg/kg I.V. | ULCER CAUSED BY STRESS ED50 mg/kg I.M. |
| COMPOUND 1 | 45 | 42 | 135 |
| COMPOUND 11 | 7 | 29 | 65 |
| COMPOUND 12 | 3 | 12 | 56 |
| CLIMETIDINE | INACTIVE (>50) | INACTIVE (>50) | INACTIVE (>75) |
| PIRENZEPINE | INACTIVE (>50) | INACTIVE (>50) | INACTIVE (>75) |

The data given in Table 2 show that the protective activity of the compounds claimed is very high even though very severe experimental conditions were used.

The two compounds used for comparison, cimetidine, which is an $H_2$ antagonistic drug, and pirenzepine, which is anticholinergic, were both inactive under the experimental conditions used.

The compounds which are the subjects of the invention, as already stated, also have interesting antagonistic activity to the release of mediators responsible for allergic reactions.

For example they show antagonism to the development of a cutaneous anaphylaxis reaction induced passively in a sensitised rat.

The method is a modification of the Goose and Blair method (Immunology 16 (1969), 749–760). Male rats weighing approximately 400 g were treated with 10 mg/kg of grade V egg albumen dissolved in 1 ml of a physiological solution by I.M. and intraperitoneal (I.P.) routes. With one mg of Freund's complete adjuvent solution. 13 days after sensitisation, the animals were killed under external anaesthesia, the blood was taken and the serum was kept at $-70°$ C. after its titre of IgE specific to egg albumen had been assayed. On the basis of type, 2 intradermal injections (i.d.) of 0.1 ml of the antiserum, titrated and suitably diluted were given into the shaved backs of 200 g male rats at a time $-24h$.

At the time 0, 5 mg/kg of physiological solution containing 25 mg/kg of antigen and 3 mg/kg of Evans blue were injected I.V.

The products under test were administered I.V. 20 minutes of the antigen. The animals were killed 30 minutes after the challenge, the skin of the back was turned inside out and the larger and smaller diameters of each blemish were measured. In practice the response of each animal was evaluated as the average of four diameters. The compounds were administered in different doses (generally 5 animals per dose per group) so as to enable a 50 effective dose (ED50) to be calculated, that is the dose which is capable of reducing the passive cutaneous anaphylaxis reaction (PCA) in the animals treated by 50% compared with the controls.

The results thus obtained are given in Table 3.

TABLE 3

| EFFECT ON A PASSIVE CUTANEOUS ANAPHYLAXIS (PCA) IN RATS | | | |
|---|---|---|---|
| COMPOUND | DOSE (mg/kg I.V.) | % inhibition | ED50 |
| COMPOUND 1 | 50 | 20.0 | 127.9 |
| | 100 | 37.2 | |
| | 150 | 58.2 | |
| COMPOUND 11 | 50 | 53.3 | 42.6 |
| | 100 | 66 | |
| | 150 | 74.7 | |
| COMPOUND 12 | 10 | 39.0 | 30.9 |
| | 30 | 45.3 | |
| | 100 | 67.6 | |

TABLE 3-continued
EFFECT ON A PASSIVE CUTANEOUS ANAPHYLAXIS (PCA) IN RATS

| COMPOUND | DOSE (mg/kg I.V.) | % inhibition | ED50 |
|---|---|---|---|
| Di-sodium chromglycate (DSCG) | 50 | 16.0 | 153.3 |
|  | 100 | 22.1 |  |
|  | 150 | 57.5 |  |

From the results obtained it can be seen that the most active compounds of the invention had antiallergic activities in the PCA test approximately 4 times greater than that of DSCG which was taken as the reference drug.

The results obtained from the PCA test were confirmed by an anaphylaxis test carried out in vitro on actively sensitised guinea-pig lung fragments.

The method is a modification of the W. E. Broklehurst method °J. Phisiol.151 (1960), 416–435é. Male guinea pigs weighing approximately 250 g were sensitised with 100 mg/ml of grade V egg albumen dissolved in 1 ml of physiological solution and administered (1 ml/kg) I.P. and subcutaneously (S.C.). After three weeks the animals were killed under ethereal anaesthesia by bleeding. The lungs were removed and immersed in Tyrode solution at 4° C. Homogeneous fragments approximately 2 mm long were cut and divided into test pieces containing approximately 400 mg of tissue and 0.8 mg of Tyrode. The samples were preincubated at 37° C. for 15 minutes with the compounds under test dissolved in 0.1 of Tyrode and incubated for a further 20 minutes at 37° C. The reaction was stopped by cooling in ice.

The histamine released by the anaphylactic reaction was extracted by the method of Shire et al. °J. Pharmacol. Exp. Ther. 127 (1959), 182é. 0.8 ml of the supernatant liquid were treated with perchloric acid and centrifuged to remove the proteins. The supernatant liquid was then made alkaline with 5N NaOH, the histamine was extracted with n-butanol and, after suitable dilution with n-heptane, was extracted again in dilute HCl.

O-phthalaldehyde was added to the samples and their fluorescence was measured with a fluorimeter at 450 mu after activation at 360 mu.

The histamine concentration in the samples was obtained from a standard straight-line graph in the range 50–800 ng/ml of histamine.

The compounds were tested at various concentrations so as to enable a 50% effective concentration (EC50) to be calculated, that is a concentration capable of reducing the release of histamine induced by the addition of egg albumen to previously-sensitised guinea-pig lung samples by 50% in comparison with the control group.

The results obtained are given in Table 4.

TABLE 4
EFFECTS ON ANAPHYLAXIS "IN VITRO" WITH ACTIVELY-SENSITISED GUINEA-PIG LUNG FRAGMENTS.

| COMPOUNDS | Concentrations (mcg/ml) | % inhibition | EC50 (mcg/ml) |
|---|---|---|---|
| COMPOUND 11 | 10 | 11.8 | 216 |
|  | 30 | 27.2 |  |
|  | 100 | 42.4 |  |
|  | 300 | 53.3 |  |
| COMPOUND 12 | 10 | 22.8 | 93 |
|  | 30 | 28.4 |  |
| Di-sodium chromoglycate (DSCG) | 100 | 56.2 | 1455 |
|  | 300 | 65.4 |  |
|  | 10 | 6.8 |  |
|  | 30 | 19.7 |  |
|  | 100 | 17.8 |  |
|  | 300 | 41.2 |  |

It can be seen from the results shown in Table 4 that some of the compounds of the invention, that is compounds 11 and 12, were 10–15 times more active in this in vitro anaphylaxis model than the reference drug, DSCG, whose activity seems to be poorly dose-related and whose effect at all doses tested never exceeded a 50% inhibitory effect on the release of histamine.

The experimental data set out above show that the compounds of the invention may be considered as a considerable therapeutic innovation for the treatment of some pathological conditions of the gastro-duodenal tract such as, for example, gastric and duodenal ulcers, ulcerative colitis, etc. In fact they combine low toxicity with considerable antagonistic activity towards gastric acid secretion induced by various antagonists such as pentagastrin, histamine and carbachol and an equally powerful cytoprotective effect. The therapeutic activity seems to be displayed through a dual protective mechanism by inhibiting the formation of excess gastric acid under the stimulus of different agents and by protecting the mucous membrane either directly, as in the case of aggressive agents such as ethanol or hypertonic NaCl solution, or by means of an indirect defense mechanism as in the case of the ulcer resulting from containment which is considered a typical ulcer of phsychogenic origin.

Moreover, if this cytoprotective activity and the antiallergic activity displayed in the experimental anaphylaxis tests in vitro and in vivo are considered, one can foresee the favourable use of the compounds of the invention for the treatment of pathological conditions sustained by an allergic component such as, for example, bronchial asthma or rhinitis or allergic conjuctivitis. Pathological conditions in which the compounds of the invention could act by a mechanism similar to the cytoprotective mechanism, by the stabilisation of the cell membranes, the stabilisation preventing the release of chemical mediators which, at the muscular level terminate in an inflammatory process, and at pulmonary level in a bronchospastic reaction.

We claim:

1. Pharmaceutically active derivatives of N-phenyl-benzamide having the formula (I)

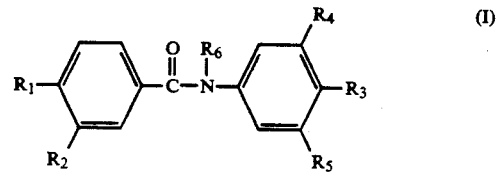

in which $R_1$ is a cyano, nitro, halogen, hydroxy, $C_1$–$C_4$ alkyl, methoxy or tetrazol-5-yl group, $R_2$ is a hydrogen, hydroxy, or methoxy group, $R_3$ is a tetrazol-5-yl group or hydrogen, $R_4$ and $R_5$ are hydrogen if $R_3$ is tetrazolyl or $R_4$ and $R_5$ are independently selected from the group consisting of carboxy, methoxycarbonyl, ethoxycarbonyl and carbamoyl if $R_3$ is hydrogen, and $R_6$ is hydrogen or methyl, and their pharmaceutically acceptable salts.

2. Derivatives of N-phenylbenzamide according to claim 1, of formula (I) in which $R_1$ is selected from the cyano group and the tetrazol-5-yl group, in which $R_2$ is hydrogen, $R_3$ is a tetrazol-5-yl group if $R_4$ and $R_5$ are hydrogen or $R_3$ is hydrogen if $R_4$ and $R_5$ are both carboxy groups.

3. A derivative of N-phenylbenzamide according to claim 1, of formula (I), in which $R_1$ is the cyano group, $R_2$, $R_4$ and $R_5$ are hydrogen and $R_3$ is the tetrazolyl group.

4. A derivative of N-phenylbenzamide according to claim 1, of formula (I), in which $R_1$ is the cyano group, $R_2$ and $R_3$ are hydrogen and $R_4$ and $R_5$ are both carboxy groups.

5. A derivative of N-phenylbenzamide according to claim 1, of formula (I) in which $R_1$ and $R_3$ are both the tetrazol-5-yl group and $R_2$, $R_4$ and $R_5$ are hydrogen.

6. Pharmaceutical compositions including a compound according to claim 1 or a pharmaceutically acceptable salt thereof as the active ingredient and a pharmaceutically accaptable carrier.

7. A method comprising administering to a patient in need of treatment of a gastrointestinal disorder characterized by excessive secretion, a therapeutically effective amount of an N-phenylbenzamide derivative of claim 1.

8. A method comprising administering to a patient in need of treatment of allergic disorders resulting from antigen-antibody reactions or from mediators of an immune response, a therapeutically effective amount of an N-phenylbenzamide derivative of claim 1.

* * * * *